United States Patent
Ogrezeanu et al.

(10) Patent No.: US 7,521,931 B2
(45) Date of Patent: Apr. 21, 2009

(54) FIBER TRACKING PHANTOM

(75) Inventors: George Ogrezeanu, Frankfurt (DE); Andreas Hartlep, Naring (DE)

(73) Assignee: BrainLAB AG, Feldkirchen (DE)

(*) Notice: Subject to any disclaimer, the term of this patent is extended or adjusted under 35 U.S.C. 154(b) by 677 days.

(21) Appl. No.: 11/318,346

(22) Filed: Dec. 23, 2005

(65) Prior Publication Data

US 2006/0195030 A1    Aug. 31, 2006

Related U.S. Application Data

(60) Provisional application No. 60/638,733, filed on Dec. 23, 2004.

(51) Int. Cl.
*G01V 3/00* (2006.01)
(52) U.S. Cl. ...................... 324/317; 324/318
(58) Field of Classification Search .......... 324/317, 324/318, 306
See application file for complete search history.

(56) References Cited

U.S. PATENT DOCUMENTS

| | | | |
|---|---|---|---|
| 6,720,766 B2 | 4/2004 | Parker et al. | |
| 6,744,039 B1 | 6/2004 | DiFilippo | |
| 7,078,897 B2* | 7/2006 | Yablonskiy et al. | 324/307 |
| 2005/0007100 A1* | 1/2005 | Basser et al. | 324/200 |
| 2008/0265882 A1* | 10/2008 | Wiggins | 324/308 |
| 2008/0284437 A1* | 11/2008 | Yoo et al. | 324/318 |

OTHER PUBLICATIONS

Leemans et al., "A Simulated Phantom for Diffusion Tensor MRI Fiber Tracking", 2003, pp. 281-285.
Imaging Quality Control, Phantom Applications and Technology Overview; Computerized Imaging Reference Systems.

* cited by examiner

*Primary Examiner*—Louis M Arana
(74) *Attorney, Agent, or Firm*—Renner, Otto, Boisselle & Sklar, LLP

(57) ABSTRACT

A phantom for use with diffusion tensor imaging includes a container and a plurality of structures within the container. The structures have anisotropic properties, wherein when the phantom is subjected to diffusion tensor imaging, the structures provide data that is recognized as fiber bundles. The structures can be formed, for example, from cloth tape, silk, wood, glass fibers cord (synthetic and viscose) and/or microfibers.

28 Claims, 6 Drawing Sheets

FIBER TRACKING PHANTOM

RELATED APPLICATION DATA

This application claims priority of U.S. Provisional Application No. 60/638,733 filed on Dec. 23, 2004, which is incorporated herein by reference in its entirety.

FIELD OF THE INVENTION

The present invention relates generally to phantoms for simulating anisotropic diffusion and for evaluating medical imaging equipment and, more specifically, diffusion tensor imaging systems.

BACKGROUND OF THE INVENTION

Diffusion tensor imaging (DTI) is a variation of magnetic resonance imaging (MRI) and allows the observation of molecular diffusion in tissues in vivo and, therefore, the molecular organization in tissues. Presently, DTI is the only method available to study in vivo and non-invasively the architecture of axonal fibers in the central nervous system.

In DTI, several sets of diffusion weighted images are acquired with the diffusion gradients applied in different directions. This allows quantitative measurements of the anisotropic diffusion of molecules in biological tissue, and this diffusion anisotropy reflects the presence of spatially oriented structures (e.g., the myelinated axonal fibers running in parallel). The molecular mobility in the spatially oriented structures is not likely to be the same in all directions. For instance, diffusion along the fibers is more pronounced than diffusion transverse to the length of the fibers.

DTI measurements involve MRI scans of a target area, e.g., a portion of the brain. As DTI systems are developed, tested and/or placed in operation, their accuracy must be verified (i.e., calibrated) to ensure accurate results and safe operation of the systems. Generally speaking, calibration and/or test measurements are performed using a phantom. As is known in the art, a phantom is any structure that contains one or more tissue substitutes, and generally is used to simulate the human body. A tissue substitute is defined as any material that simulates a body of tissue.

Numerous phantoms have been developed for various imaging techniques. For example, U.S. Pat. No. 6,744,039 relates to a fillable phantom for use with nuclear imaging. More specifically, the phantom includes a container, a porous medium within the container, and a connector for filling the container with a radioactive solution. One or more contrasting regions formed in the porous medium are in fluid communication with the porous medium in order to absorb the radioactive solution. The phantom provides radioactive hot spots within a less radioactive background.

U.S. Pat. No. 6,720,766 relates to a thin film phantom for testing and measuring the performance of magnetic resonance imaging (MRI) and x-ray computed tomography (CT) imaging systems. The phantom includes a planar medium and a plurality of individually sub-resolvable scatters having pre-selected magnetic resonance properties within a pattern of resolvable regions on the surface of the medium. The phantom can be used to check the quality of images obtained from the MRI and CT systems.

U.S. Pat. No. 6,409,515 describes a phantom for a real-time interactive imaging system. The phantom includes a plurality of segments having unique identifiers, the segments joining together to form a polyhedron around an inner plate. In one embodiment, the inner plate has a unique identifier and two inner blocks positioned orthogonally upon it, each inner block also having a unique identifier. The phantom provides a variety of uniquely identified surfaces, angles and edges for scanning practice in a real-time interactive environment, and enables the imaging system user to verify image correctness and annotation.

SUMMARY OF THE INVENTION

The above discussed prior art describe phantoms for various imaging techniques, including CT, MRI and nuclear imaging. The above prior art, however, does not disclose a phantom for use with DTI systems. The present invention provides such a phantom for use with DTI systems.

According to one aspect of the invention, a phantom for diffusion tensor imaging (DTI) comprises one or more fiberous structures through which a; fluid can diffuse anisotropically for simulation of diffusion in a body of tissue of an animal. Accordingly, a diffusion tensor image of the phantom can be obtained to provide data having correlation to the tissue under investigation.

In an embodiment, the one or more fiberous structures are elongated to form a fiber tracking phantom. The one or more fiberous structures are carried on a support of any desired configuration. The support can simply be a plate, but more preferably is in the form of a container having side walls on which the elongated structures are supported. When the phantom is subjected to diffusion tensor imaging, the elongated structure or structures provide data that is recognized as a fiber bundle or bundles.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed.

DETAILED DESCRIPTION

Figure 1:
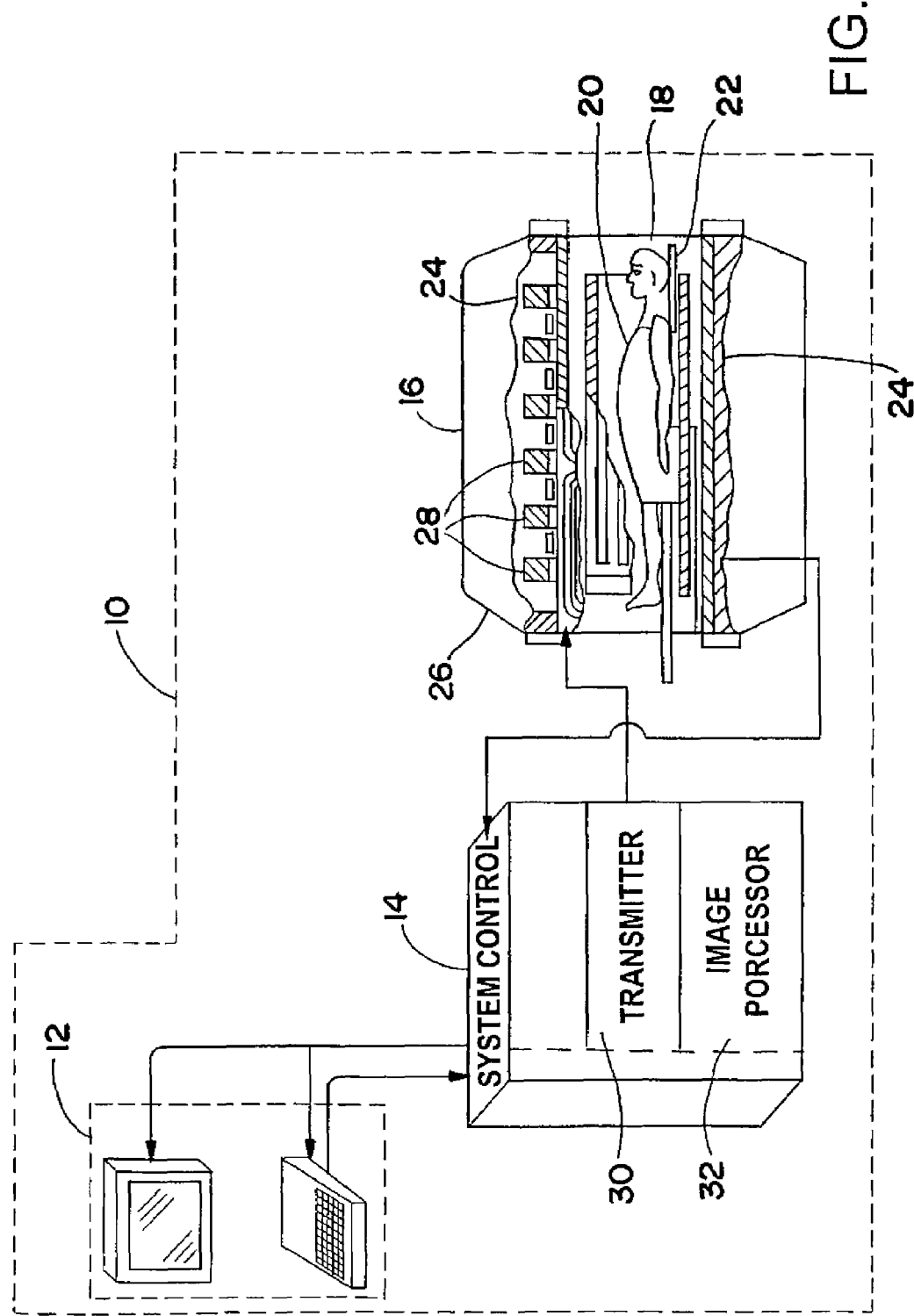
FIG. 1 is a schematic diagram of a magnetic resonance imaging system.

Referring to FIG. 1, major components of an MRI imaging system 10 include an operator console 12 from which an operator controls the imaging system 10. A system control 14 receives commands from the operator indicating the scan sequence to be performed and transmits imaging control signals to an MRI scanner 16. Within a cylindrical bore 18 of scanner 16, patient or object 20 is positioned on a table 22 and is surrounded by a magnetic coil or detector 24. Magnetic coil 24 is part of a magnet assembly 26, which also includes a polarizing magnet 28. Polarizing magnet 28 subjects object 20 to a uniform magnetic field. A transmitter or source 30 included in system control 14 transmits radio frequency pulses to magnet assembly 26. The resulting signals emitted by the excited spins in object 20 are picked up by magnetic coil 24, transmitted to system control 14 and reconstructed into an image by an image processor 32. The operator of imaging system 10 is able to view the image on console 12. If imaging system 10 is interactive in real time, the operator is able to view images and alter the scan sequence as it progresses.

Water molecules move through and within tissue of a patient's body by diffusion, which also is known as Brownian movement. Brownian movement is the random movement of microscopic particles suspended in a liquid or gas, and is caused by collisions with molecules of the surrounding medium.

As the water molecules move within and through tissue, they usually do so anisotropically, i.e., at different rates in one direction than in other directions. Some materials exhibit these anisotropic properties, i.e., diffusion occurs faster in one direction than in other directions. The wider the variation in diffusion rate as a function of direction, the more anisotropic the material is said to be.

Figure 2:
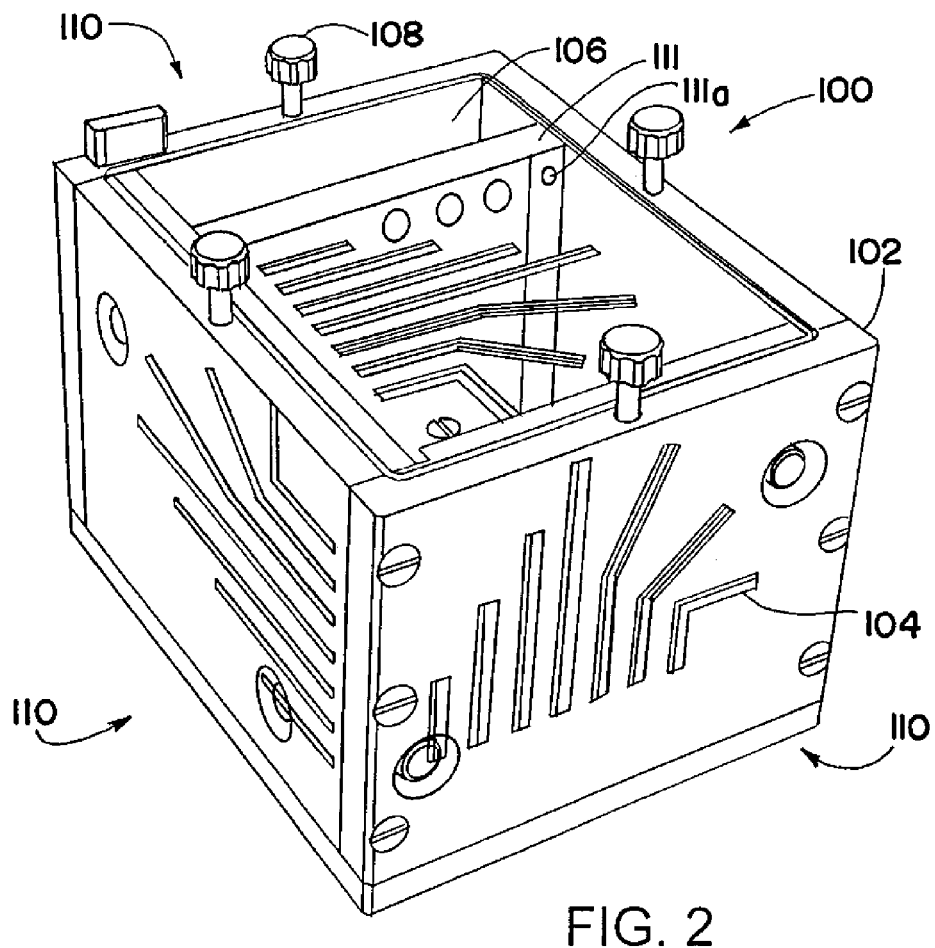
FIG. 2 is a perspective view of an exemplary phantom in accordance with the invention.

FIG. 2 shows an exemplary DTI phantom 100 according to the present invention. The phantom 100 comprises a support 102 and one or more artificial structures 104 through which a fluid can diffuse anisotropically for simulation of diffusion in a body of tissue of an animal. The artificial structures can be fiberous structures, as described in more detail below. Accordingly, a diffusion tensor image of the phantom can be obtained to provide data having correlation to the tissue under investigation.

In the illustrated embodiment, the one or more anisotropic structures 104 are elongated to form a fiber tracking phantom. The one or more artificial structures 104 are mounted to the support 102 which can be of any desired configuration. The support 102 can simply be a plate, but more preferably is in the form of a fillable container as shown, and the elongated structures are mounted to the side walls of the container and within a chamber defined by the container. When the phantom is subjected to diffusion tensor imaging, the elongated structure or structures provide data that is recognized as a fiber bundle or bundles.

As used herein, anisotropic structures are structures that exhibit variable diffusion within the structure. For example, diffusion in the anisotropic structure may occur faster in one direction than in another direction. The phantom 100, when utilized in conjunction with DTI, provides a model that can be used to create artificial diffusion data, that can be recognized as one or more fiber bundles. A fiber bundle, as used herein, refers to a group of elongated, thread-like structures formed in bundles or tracts of fibers.

Structures 104 formed from fibers or fiber bundles create a plurality of tracts (i.e., small pathways) through which diffusion can occur. The plurality of tracts or "diffusion tracts" minimize transverse diffusion within the structure, thereby enhancing the DTI characteristics of the structure 104. Preferably, the materials used to form the structures 104 are tightly packed or tightly bundled together, thereby increasing the density of the structure and the number of diffusion tracts within the structure 104.

The container 102 can be formed from any suitable material, such as plexiglass, and can be formed, for example, from segments, such as plates, suitably joined together to form the container. In the exemplary embodiment, plexiglass segments are bonded and/or fastened together to form the container. A top wall (cover) 106 of the container 102 can be removed via quick release fasteners 108, thereby permitting access to the inside of the container 102. As will be appreciated, the container 102 can be formed using other magnetic resonant (MR) compatible materials, such as plastics, non-ferrous metals, and the like. Additionally, while the container is illustrated as a cube, other shapes, such as a sphere, an ellipsoid, a hemisphere, etc., can be implemented without departing from the scope of the invention.

Figure 3:
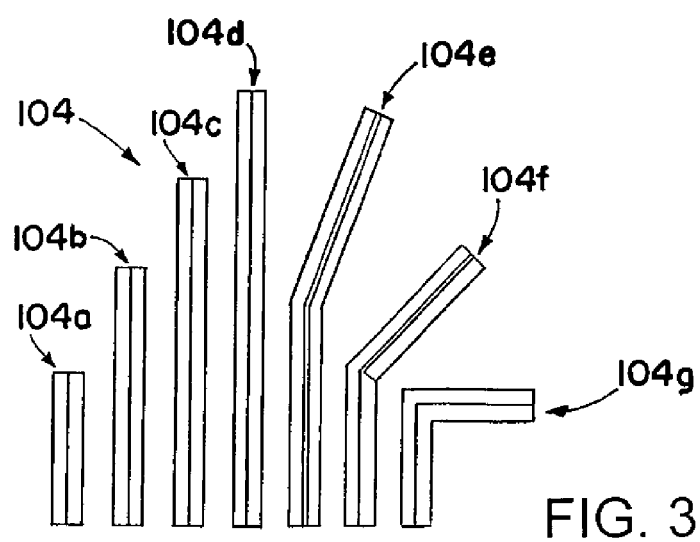
FIG. 3 is a schematic drawing of exemplary elongated structures used in the phantom showing the variation in length and angulation in accordance with the invention.

With additional reference to FIG. 3, the structures 104 are shown as elongated segments having various lengths and angulations. For example, the structures 104a-104d include only straight segments, while the structures 104e-104g include two straight segments placed at an angle with respect to each other. The length and angulations of the structures 104 can vary depending on the design requirements of the phantom. Preferably, the phantom includes a number of straight and angled structures 104 to provide an accurate representation of the simulated tissue, e.g., brain tissue. According to one embodiment, the segments are between about 2 centimeters and about 8 centimeters in length, and the angulations are between about 30 degrees and 90 degrees.

The cross section of each structure 104 can be any shape, although circular and rectangular cross sections are preferred due to their ease of fabrication. Structures 104 having circular cross sections, for example, can be between about 1 millimeter to about 8 millimeters in diameter. Structures having other cross sections, e.g., square, rectangular, elliptical, etc., can have dimensions that fall in about the same range, e.g., a rectangular cross section having a height of 2 mm and a length of 4 mm.

The structures 104 are fixed in the container 102 so as to minimize or inhibit motion of the structures. For example, the structures 104 can be fixed to the side walls of the container 102 using an adhesive, e.g., a hot-melt adhesive. Other means of bonding the structures 104 to the container 102 could be used, such as solvent-bonding, for example. As a further alternative, the structures 104 could be clamped or otherwise supported within the container using MR compatible mechanical fasteners, such as screws or clamps fabricated from non-ferrous and/or plastic materials.

In the exemplary embodiment of FIG. 2 only three groups 110 of structures 104 are illustrated. It will be appreciated, however, that fewer or more groups 110 of structures 104 can exist within the phantom 100, and for sake of clarity, only three groups are shown.

Once the structures 104 are disposed within the container 102, a liquid, such as water or glycerine, can be added to the container 102 and the container can then be sealed. Since the structures 104 exhibit anisotropic properties, the liquid begins to diffuse into the structures 104 at various rates and/or directions along the structures 104. More specifically, the liquid molecules move or diffuse between the fibers of the structure in a longitudinal direction, but generally not through or across the fibers. This restricted diffusion mimics diffusion within tissue, such as brain tissue.

Figure 4:
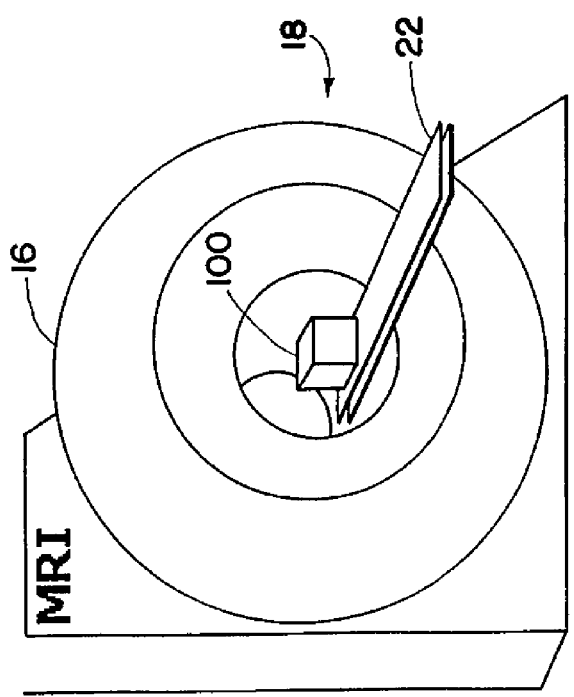
FIG. 4 illustrates an isometric view of the phantom placed within the magnet bore of a magnetic resonance scanner.

The phantom 100 then is placed within an MR scanner as shown in FIG. 4, and images of the phantom are obtained using various data sets, e.g., weighted and unweighted image series, different diffusion directions, etc. Once the DTI scans are obtained, the images can be reviewed to determine optimal scan settings, performance characteristics of the scanner, comparison trials between different scanners, and/or calibration of the scanner system.

Optionally, baffles 111 can be placed within the container, as shown in FIG. 2. As will be described in more detail below, the baffles 111 inhibit liquid motion, thereby providing improved imaging. The baffles can comprise one or more plates arranged substantially parallel to one another within the container 102, wherein the baffles 111 have openings 111a formed therein. Preferably, the openings between adjacent baffles are staggered, such that openings 111a on adjacent baffles are on different vertical and/or horizontal planes. The baffles preferably are formed from MR compatible materials, such as non-ferrous metals, plastics and the like. As will be appreciated, other types of baffles can be implemented without departing from the scope of the invention.

The structures 104 are formed using materials having anisotropic properties. By way of example, the structures 104 can be formed from silk (as a bundle or texture), glass fiber (as a bundle), wood, and cord string (viscose and synthetic). When examining DTI scans of these materials, they were found to exhibit diffusion characteristics similar to those of the human brain. As should be appreciated, other materials that exhibit diffusion characteristics similar to the human brain (or to a specific target region), also may be used without departing from the scope of the invention.

As will be appreciated, the number of diffusion directions within the phantom 100 varies with the number of structures 104 within the phantom 100. As the number of structures 104 increases, the number of image data obtained during a DTI scan also increases. This additional data can be used to verify the results of testing and/or calibration of the DTI system.

Figure 5:
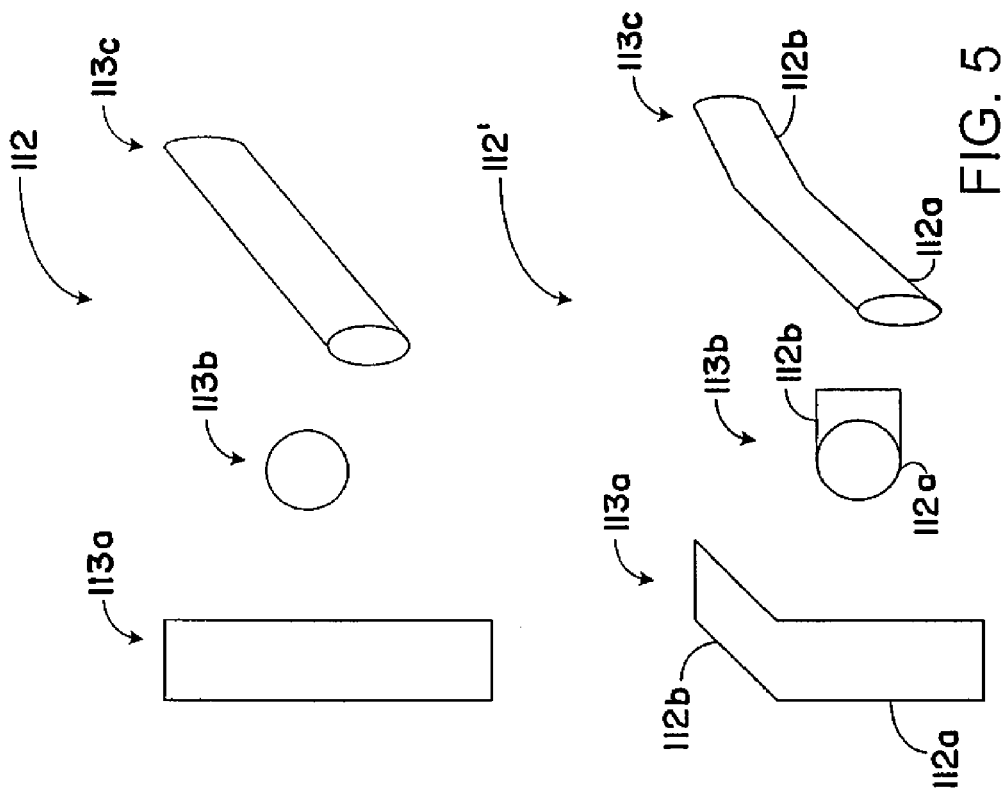
FIG. 5 is a top and cross-sectional view of several exemplary vessels in accordance with the intention.

Prior to discussing each of the aforementioned materials, it is noted that some of the materials (e.g., silk and cord) are not rigid materials (i.e., they will not support themselves in a fixed position) and, therefore, these materials can be contained within a vessel. More specifically, these materials are bundled and surrounded by the vessel to define the structure 104. The vessel operates to provide a defined shape, length and angulation of the material and thus of the structure 104. The vessel can be formed from any MR compatible material. According to one embodiment, the vessel is a cylindrical structure formed from a plastic material, such as a plastic straw, for example. FIG. 5 illustrates several exemplary vessels 112, 112', including a top view 113a, a side view 113b and an isometric view 113c. The vessel 112 is a straight segment having a circular cross section, while the vessel 112' includes a first segment 112a formed at an angle with respect to a segment section 112b. Both the first and second segments 112a, 112b have circular cross sections. As will be appreciated, the vessels can have different cross-sections and different configurations depending on the application.

As was noted above, several materials can be used to form the structures. These materials are described in more detail below.

Leukosilk

Leukosilk is the trade name of Beiersdorf AG for a white surgical tape fabricated from acetate fabric. Other adhesive silk or silk-like materials that exhibit a fine webbed texture, such as Askina Silk, which is the trade name of B. Braun AG, and Omnisilk, which is the trade name of Paul Hartmann AG, also can be used with similar results. Such materials are collectively referred to herein as cloth tape.

Figure 6A:
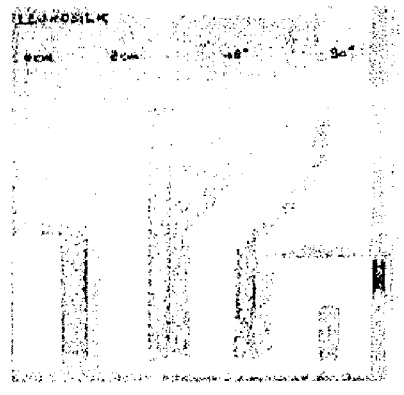
FIG. 6A illustrates an exemplary structure formed from Leukosilk in accordance with the invention.

In using Leukosilk as a material for the structures 104, multiple layers, such as about 20 layers, of Leukosilk can be placed one on top of the other to form a plurality of structures having the shapes illustrated in FIG. 6A. The shape of the Leukosilk structures 104 can be obtained by cutting strips of the multi-layered Leukosilk and bonding the strips together. The ends of the strips can be cut at oblique angles as required to define the angulation of the structure.

Figure 6B:
FIG. 6B illustrates the diffusion tensor image for the structure of FIG. 6A.

A sample of structures 104 formed using Leukosilk 120 is shown in FIG. 6A, and the corresponding DTI scan is shown in FIG. 6B. As can be seen from FIG. 6B, the Leukosilk texture 122 can be visualized using the DTI scan. However, the fibers can be seen to be partially missing along regions 124 of the Leukosilk 120 due to air bubbles (the adhesive substrate of the Leukosilk that was employed was not water resistant). Additionally, the fibers typically are very short and do not project in a single direction due to the textile structure of the Leukosilk 120. The Leukosilk can be pressed together to remove air bubbles, thereby providing a material that can be used to represent flat structures 104.

Silk

Figure 7A:
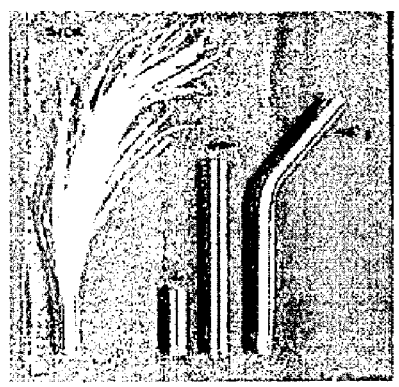
FIG. 7A illustrates an exemplary structure formed from silk in accordance with the invention.
Figure 7B:
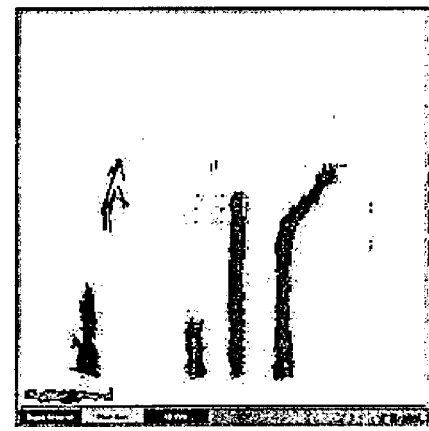
FIG. 7B illustrates the diffusion tensor image for the structure of FIG. 7A.

As was noted above, structures 104 formed using silk are created in a vessel 112, 112'. With reference to FIGS. 7A-7B, silk threads 130 are fed into the vessel 112, 112', thereby defining the length and shape of the structure 104. According to one embodiment, the silk structure 104 is formed from small threads of silk, e.g., silk dental floss or the like. In the exemplary embodiment of FIG. 7A, portions 132 of the silk 130 were left outside the vessel 112 to see the effect of loose threads with respect to compacted threads.

FIG. 7B illustrates the DTI scan using a silk structure 104. As can be seen from the DTI scan, both straight fibers 134 and angulated fibers 136 can be detected by the DTI scan. The loose portions 132 outside the vessel 112, 112', however, are not sufficiently compacted to produce a satisfactory diffusion signal. Additionally, and as can be seen in FIG. 7B, the silk structures 104 do not exhibit significant skewing due to air bubbles within the vessel.

Glass Fiber

Figure 8A:
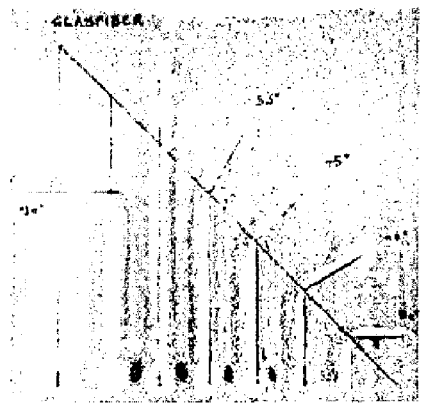
FIG. 8A illustrates an exemplary structure formed from glass fiber in accordance with the invention.

With reference to FIG. 8A, the glass fibers 140, such as Glass roving 2400 tex manufactured by R&G GmbH, are twisted together to form a larger thread of fiber and, therefore, are not placed within a vessel. Elimination of the vessel eliminates the possibility of air bubbles between the vessel and the fibers. On the other hand, elimination of the vessel also results in a fiber structure that is somewhat more loosely compacted than would be the same fiber structure within a vessel. In an alternative embodiment, the glass fibers can be placed in a vessel 112, 112' (without twisting the fibers together) as discussed above with respect to the silk fibers 134. The glass fibers 140 have similar capillarity as the silk fibers 134.

Figure 8B:
FIG. 8B illustrates the diffusion tensor image for the structure of FIG. 8A.

Twisting of glass fibers 140 changes the structure of the fibers. More specifically, twisting the glass fibers together creates a spiral structure. As can be seen in FIG. 8B, the DTI scan detects several fibers 142. However, the overall fiber length is reduced.

Wood

Figure 9A:
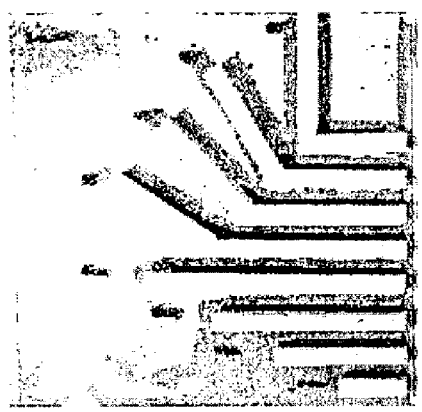
FIG. 9A illustrates an exemplary structure formed from wood in accordance with the invention.

With reference to FIG. 9A, structures 104 formed from balsa wood 150 are illustrated. Balsa wood is very soft and light with a coarse open grain. The density of balsa wood ranges from 100-200 $kg/m^3$. The cells within balsa wood are large and very thin walled, so that the ratio of solid matter to open space is small. About 40% of the volume of a piece of balsa is solid substance, and the reminder being water and other non-solid material. Other woods, such as bamboo, also can be used to form the structures 104.

Figure 9B:
FIG. 9B illustrates the diffusion tensor image for the structure of FIG. 9A.

The water concentration in the sample balsa wood 150 was low and, therefore, the diffusion signal obtained from the DTI scan also was low. As a result, the liquid diffusion was only 1 millimeter deep into the balsa wood 150. Also, air inside the balsa wood produced strong artifacts 152 in the DTI scan. Freshly cut balsa wood is believed to yield better results than those illustrated in the DTI scan. Nevertheless, recognizable features 154 of the balsa wood structure 104 can be identified, as shown in FIG. 9B.

Viscose and Synthetic Cord

Figure 10A:
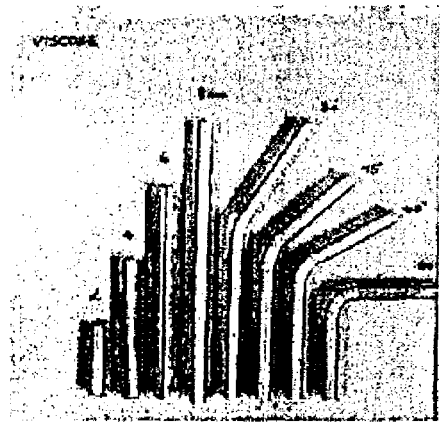
FIG. 10A illustrates an exemplary structure formed from viscose in accordance with the invention.
Figure 10B:
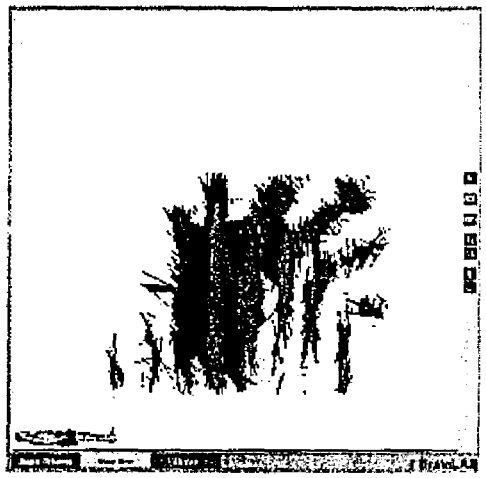
FIG. 10B illustrates the diffusion tensor image for the structure of FIG. 10A.
Figure 11A:
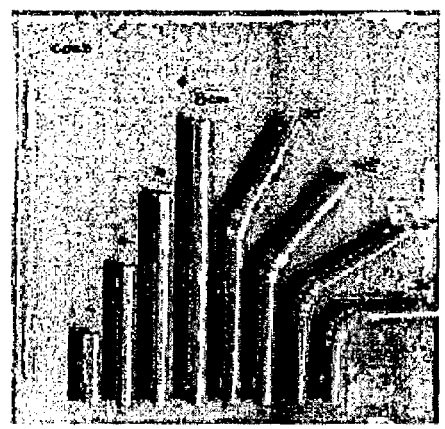
FIG. 11A illustrates an exemplary structure formed from synthetic cord in accordance with the invention.
Figure 11B:
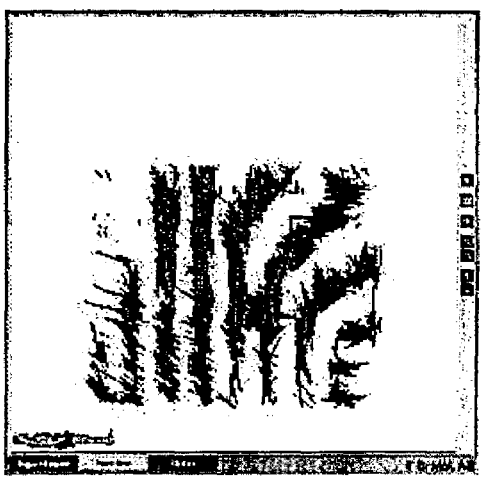
FIG. 11B illustrates the diffusion tensor image for the structure of FIG. 11A.

FIG. 10A illustrates structures 104 formed from viscose 160 (also referred to as Rayon), which is a natural polymer made from wood pulp and exhibits highly absorbent properties. FIG. 11A illustrates structures formed from synthetic cord 170. Both the viscose and the synthetic cord were formed within a vessel 112, 112', which provides the shape and length for the structure and compacts the viscose and cord into tight bundles. As was described above, the formation of air bubbles within the structures 104 is minimized by introducing each respective material (viscose or synthetic cord) into the vessel 112, 112' under water, for example. FIG. 10B shows the resulting DTI scan of the viscose structures 104, while FIG. 11B shows the resulting DTI scans for the synthetic cord structures 104. As can be seen in the DTI scan, straight as well as curved fibers or tubes can be recognized for both the viscose and synthetic cord structures.

Microfibers

Microfibers are fibers that include strands thinner than one denier. As is known by those skilled in the art, a denier is a unit of fineness for fibers based on a standard mass per length of 1 gram per 9,000 meters of yarn. Thus, the larger the denier, the thicker the fiber.

Silk, which was discussed above, has about 1.24 deniers and provides good fiber tracking results. Microfibers generally are less than 0.9 denier, and typically are between 0.5 to 0.6 deniers. Various types of microfibers are available on the market, and exemplary types are provided below.

| Microfiber Name | Manufacturer |
| --- | --- |
| Trevira Finesse polyester | Hoechst Celanese |
| Trevira Micronesse | Hoechst Celanese |
| Trevira Micro | Hoechst Celanese |
| Silky Touch nylon | BASF Corp. |
| Sportouch | BASF Corp. |
| MicroSupreme acrylic | Sterline Fibers Inc. |
| Dacron polyester microfiber | DuPont |
| Supplex Micro nylon | DuPont |
| Micromattique polyester | DuPont |
| Tactel Micro nylon | DuPont |
| Micro Modal rayon | Lenzing |
| MicroSpun polyester | Wellman |

Microfibers are advantageous in that the thinner fibers will allow a higher concentration of fibers in a bundle and, thus, when subject to DTI, will produce a higher water diffusion signal. Further, since the microfibers are substantially lighter than the previously discussed fibers, the number of artifacts and/or an amount of distortion in the image is reduced.

The materials described above provide varying results in the diffusion tensor measurements, as can be seen in the DTI scans. The differences between materials can be attributed to several factors, including liquid motion, air bubbles, image noise and water content. As is known in the art, image noise is a by-product of the MR scan and, therefore, will not be discussed herein. The remaining three factors are discussed below.

Liquid Motion

As was noted above, the phantom 100 is filled with a liquid and placed on an MRI table 22 to simulate a patient's head (or other body part) during an MR scan. During the MR scan, the table 22 (including the phantom 100) is moved to various positions. This movement can cause the liquid within the phantom 100 to move about, thereby creating waves which can produce image artifacts. Such liquid movement can be minimized, for example, by implementing baffles within the container to restrict liquid motion and, therefore, minimize the waves. Additionally, waves can be minimized by ensuring that the container 102 is completely filled with liquid, thereby eliminating any space within the container in which liquid motion could occur. Alternatively, the viscosity of the liquid can be modified to minimize liquid motion as the phantom is moved and/or rotated, or liquid motion can be reduced by using a solid liquid such as a gelatin, silicon or petroleum jelly.

Air Bubbles

The vessels 112, 112' used to form the silk and cord structures 104 can contain small air bubbles between the material and the vessel wall. Since diffusion will not take place within the air bubble, these areas will not image. The air bubbles can be minimized by feeding the material (e.g., silk and/or cord structures) into the vessel 112, 112' while the vessel is submersed in the liquid, e.g., under water. Nevertheless, some small air bubbles still can become trapped within the vessel 112, 112'. Other techniques of combining the material within the vessel 112, 112' can be implemented to further reduce the likelihood of air bubbles in the structure 104. For example, the vessel can be formed using a vacuum process, wherein air bubbles are actively removed from the vessel.

Water Content

DTI requires that the liquid molecules, e.g., water molecules, move through the tissue (or the structure 104), in order to obtain satisfactory images. If the water concentration within the structure 104 is insufficient, the diffusion signal may be weak or reduced. This is more prevalent for structures 104 formed using balsa wood, as the liquid does not completely penetrate such structures and/or the balsa wood may have lost much of its water content.

The wood structures 104 provide satisfactory DTI for regions that are in contact with the liquid, e.g., regions at the outer edges of the structure 104. The inner regions of the wood structure, however, can provide varying results. Such variance can be minimized by using wood that has been freshly cut and/or has a naturally high water content (e.g., balsa wood). Alternatively, very fine or thinly cut pieces of wood can be used such that the liquid will substantially diffuse though the structure 104.

The phantom 100, when utilized in conjunction with DTI, provides a model that can be used to create artificial diffusion data that can be recognized as fiber bundles (or other structures). The form and size characteristics of the structures provide results similar to those obtained when imaging a human brain, for example. Additionally, the phantom 100 can be used to calibrate an MR scanner and/or the software models/mathematical algorithms implemented within the MR scanner. For example, using the MR scanner, DTI data can be acquired of the phantom 100. The obtained data then can be compared to the known structure of the phantom (location, size, angulations, etc., of the structures) and, based on the results of the comparison the software models and/or mathematical algorithms utilized in the MR scanner can be adjusted to obtain the desired result, i.e., an accurate DTI of the phantom 100.

The phantom 100 also can be used to reduce or identify artifacts within the obtained DTI data. For example, scan protocols (e.g., motion control of the scanner) can be optimized in different directions to minimize or eliminate artifacts caused by the motion. Additionally, based on the DTI data of the phantom, the number of diffusion directions required to minimize artifacting can be determined. Another application for the phantom 100 is to subject the phantom to a number of different scan conditions, e.g., varying the diffusion directions and or the scan parameters, to determine the optimal settings for scanning an actual patient. Furthermore, the phantom can be used to compare different scanner types and/or manufactures to determine which scanner provides a desired result.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A phantom for diffusion tensor imaging (DTI) comprising one or more artificial structures through which a fluid can diffuse anisotropically for simulation of diffusion in a body of tissue of an animal, whereby when the phantom is subjected to diffusion tensor imaging, the one or more artificial structures provide diffusion data.

2. The phantom of claim 1, further comprising a support on which the one or more artificial structures are supported.

3. The phantom of claim 2, wherein the support includes a container, and the one or more artificial structures are disposed within the container.

4. The phantom of claim 3, wherein the one or more artificial structures are fixed within the container using an adhesive or magnetic resonant compatible fasteners.

5. The phantom of claim 3, further comprising baffles within the container that reduce liquid motion within the container as the container is moved and/or rotated.

6. The phantom of claim 3, wherein the container is formed as a cube, a sphere, a hemisphere or an ellipsoid.

7. The phantom of claim 2, wherein the support is formed from magnetic resonant compatible materials.

8. The phantom of claim 1, wherein the one or more artificial structures is elongate.

9. The phantom of claim 1, wherein the one or more artificial structures are formed from the group consisting of cloth tape, silk, glass fiber, wood, viscose, synthetic cord, microfibers, and combinations thereof.

10. The phantom of claim 9, wherein the silk, glass fiber, viscose, synthetic cord, microfibers, or combinations thereof are bundled together to form a thread of said fibers.

11. The phantom of claim 9, wherein the silk, glass fiber, viscose, synthetic cord, microfibers, or combinations thereof are twisted together to form a thread of said fibers.

12. The phantom of claim 1, wherein the one or more artificial structures further comprise a magnetic resonance compatible vessel that defines a shape of each respective structure.

13. The phantom of claim 12, wherein silk, synthetic cord, viscose, microfibers or combinations thereof are bundled within the vessel.

14. The phantom of claim 12, wherein the vessel is a cylindrical vessel.

15. The phantom of claim 1, wherein the one or more artificial structures have a circular or a rectangular cross section.

16. The phantom of claim 1, further comprising a liquid within the container.

17. The phantom of claim 16, wherein the liquid is selected from the group consisting of water, glycerine, silicon, petroleum jelly and gelatin.

18. The phantom of claim 16, wherein the liquid has a viscosity greater than water so as to reduce liquid motion within the container as the container is moved and/or rotated.

19. The phantom of claim 1, wherein each structure is between about 2 cm and 8 cm in length.

20. The phantom of claim 1, wherein at least one structure includes a first segment oriented at an angle with respect to a second segment.

21. The phantom of claim 20, wherein the angle between the first and second segments is between about 30 degrees and 90 degrees.

22. The phantom of claim 1, wherein the artificial structures are fiberous structures.

23. A phantom for diffusion tensor imaging (DTI) comprising one or more artificial structures having a plurality of diffusion tracts through which a fluid can diffuse anisotropically for simulation of diffusion in a body of tissue of an animal, whereby when the phantom is subjected to diffusion tensor imaging, the one or more artificial structures provide diffusion data.

24. A phantom for diffusion tensor imaging (DTI) comprising one or more artificial structures through which a fluid can diffuse anisotropically for simulation of diffusion in a body of tissue of an animal, said diffusion substantially occurring along a single direction of the one or more artificial structures, whereby when the phantom is subjected to diffusion tensor imaging, the one or more artificial structures provide diffusion data.

25. A method of optimizing a DTI scanner, comprising:
    subjecting the phantom of claim 1 to a diffusion tensor scan to obtain DTI data;
    comparing the DTI data to known DTI characteristics of the phantom; and
    adjusting at least one parameter of the DTI scanner based on the comparison.

26. The method of claim 25, wherein adjusting the parameter includes adjusting a model utilized within the MR scanner based on the comparison of the DTI data and the known DTI characteristics of the phantom such that DTI images obtained using the model accurately reflect the known DTI characteristics of the phantom.

27. The method of claim 25, wherein adjusting the parameter includes adjusting a mathematical algorithm utilized within the MR scanner based on the comparison of the DTI data and the known DTI characteristics of the phantom such that the mathematical algorithm provides data that accurately reflects the known DTI characteristics of the phantom.

28. The method of claim 25, wherein adjusting the parameter includes adjusting a scan protocol of the DTI scanner based on the comparison of the DTI data and the known DTI characteristics of the phantom such that artifacts in the DTI are reduced.

* * * * *